United States Patent
Jin et al.

(10) Patent No.: US 11,116,954 B2
(45) Date of Patent: Sep. 14, 2021

(54) METHOD TO PRINT MICRONEEDLE PATCHES RAPIDLY

(71) Applicant: SHANGHAI JIAO TONG UNIVERSITY, Shanghai (CN)

(72) Inventors: Tuo Jin, Shanghai (CN); Fei Wu, Shanghai (CN)

(73) Assignee: Shanghai Jiao Tong University, Shanghai (CN)

(*) Notice: Subject to any disclaimer, the term of this patent is extended or adjusted under 35 U.S.C. 154(b) by 312 days.

(21) Appl. No.: 16/077,736

(22) PCT Filed: Feb. 14, 2017

(86) PCT No.: PCT/CN2017/073512
§ 371 (c)(1),
(2) Date: Aug. 14, 2018

(87) PCT Pub. No.: WO2017/140239
PCT Pub. Date: Aug. 24, 2017

(65) Prior Publication Data
US 2019/0046778 A1 Feb. 14, 2019

Related U.S. Application Data

(60) Provisional application No. 62/295,166, filed on Feb. 15, 2016.

(51) Int. Cl.
*A61K 9/00* (2006.01)
*A61M 37/00* (2006.01)
(Continued)

(52) U.S. Cl.
CPC ....... *A61M 37/0015* (2013.01); *A61K 9/0021* (2013.01); *A61K 47/32* (2013.01);
(Continued)

(58) Field of Classification Search
CPC ........................ A61K 9/0021; B81C 1/00373
See application file for complete search history.

(56) References Cited

U.S. PATENT DOCUMENTS

2008/0157421 A1* 7/2008 Mukai ............... A61M 37/0015
264/164
2008/0213461 A1* 9/2008 Gill ...................... A61K 9/0021
427/2.3
(Continued)

FOREIGN PATENT DOCUMENTS

CA    2943215 A    10/2015
CN    103301092 A    9/2013
(Continued)

OTHER PUBLICATIONS

International Bureau of WIPO, International Search Report and Written Opinion in Application No. PCT/CN2017/073512 dated May 12, 2017.

*Primary Examiner* — Timothy Kennedy
(74) *Attorney, Agent, or Firm* — Treasure IP Group, LLC

(57) ABSTRACT

This invention teaches a method to achieve rapid 3D printing of microneedle patches. The 3D printing method comprises a printing nozzle of multiple micro-holes and cold plate/platform on which the microneedle-supporting sheet (membrane) is placed. The solution or aqueous solution of microneedle-forming materials is printed onto the cold microneedle-supporting sheet with programed rate of injection from the nozzle and velocity of the nozzle lifting. The relationship between the injection rate and the lifting velocity determines the shape of the microneedle tips. The freshly printed microneedles on the cold sheet are dried in two ways, drying at a temperature close to the ice point of water or drying after a freeze-thaw treatment of the microneedles.

20 Claims, 2 Drawing Sheets

(51) Int. Cl.
*A61K 47/32* (2006.01)
*A61K 47/36* (2006.01)
*B81C 1/00* (2006.01)
*A61K 38/00* (2006.01)

(52) U.S. Cl.
CPC .......... *A61K 47/36* (2013.01); *B81C 1/00373* (2013.01); *A61K 38/00* (2013.01); *A61M 2037/0053* (2013.01); *B81B 2201/055* (2013.01); *B81C 2201/0185* (2013.01)

(56) References Cited

U.S. PATENT DOCUMENTS

| | | | |
|---|---|---|---|
| 2008/0299290 A1* | 12/2008 | Kirby | A61M 37/0015 427/2.28 |
| 2011/0195124 A1* | 8/2011 | Jin | A61K 9/0021 424/486 |
| 2014/0200511 A1 | 7/2014 | Boyden et al. | |
| 2015/0030642 A1* | 1/2015 | Wu | A61K 39/145 424/400 |
| 2015/0224293 A1* | 8/2015 | Jung, II | A61M 37/0015 604/272 |
| 2015/0265530 A1* | 9/2015 | Xu | A61K 38/06 604/289 |
| 2016/0158511 A1* | 6/2016 | Jin | A61K 9/0021 604/173 |

FOREIGN PATENT DOCUMENTS

| | | | |
|---|---|---|---|
| CN | 104096311 A | 10/2014 | |
| JP | 2010535591 A | 11/2010 | |
| JP | 2013172847 A | 9/2013 | |
| JP | 2016528971 A | 9/2016 | |
| KR | 20150096627 A | 8/2015 | |
| WO | 2009021048 A2 | 2/2009 | |
| WO | 2014204176 A1 | 12/2014 | |
| WO | WO-2015010599 A1 * | 1/2015 | ........... A61K 9/0021 |
| WO | 2015130900 A1 | 9/2015 | |

* cited by examiner

| | Shape | Math model | Vol% of front 60% length |
|---|---|---|---|
| Regular cone | | $Rate_{inj} = \pi r_0^2 - 2\pi r_0 bh + \pi b^2 h^2$<br>$r_0$: base radius; h: height of microneedle | 21% |
| Fat cone | | $Rate_{inj} = \pi r_0^2 - 2\pi r_0 bh^2 + \pi b^2 h^4$<br>$r_0$: base radius; h: height of microneedle | 40% |
| Arrow on waistline | | $Rate_{inj} = \{\pi r_0^2 - 2\pi r_0 bh + \pi b^2 h^2\}_0^{h/2}$<br>$Rate_{inj} = \{\pi r_0^2 - 2\pi r_0 bh^2 + \pi b^2 h^4\}_{h/2}^{h}$ | 50% |

METHOD TO PRINT MICRONEEDLE
PATCHES RAPIDLY

CROSS REFERENCE TO RELATED APPLICATIONS

This application is a U.S. National Stage entry under 35 U.S.C. § 371 based on International Application No.: PCT/CN2017/073512, filed on Feb. 14, 2017, which was published under PCT Article 21(2) and which claims priority to U.S. Provisional Application No. 62/295,166, filed on Feb. 15, 2016, which are all hereby incorporated herein in their entirety by reference.

TECHNICAL FIELD

The present invention pertains to a new process to produce microneedle arrays or patches through a none-molding method which may be named as printing, 3D printing, cumulating, or piling up. The new process will substantially improve the quality and efficiency of production of polymeric microneedles or microneedle patches.

BACKGROUND

Non-invasive delivery of protein and peptide therapeutics has been a long-standing objective for pharmaceutical development. Taking diabetes for example, to avoid the lifetime-long frequent injections, scientists in the field have contributed extensive research efforts over half century to examine variety of non-injective methods, comprising the inhalation, oral, nasal spray, needle-free injection, as well as transdermal delivery systems. However, non-injection delivery of protein and peptide medicines across our natural biological barriers remains to be a daunting task.

The invention of microneedles, an array of needles several hundreds micron in length, has provided a promising solution for cross-skin drug delivery. The tiny needles may penetrate the most impermeable layer of skin (stratum corneum or epideermis) to create diffusion channels for lipophobic molecules without causing skin injury and pain feeling. There are four types of microneedle systems available to date, solid microneedles, hollow microneedles, polymeric dissolvable microneedles, and polymeric swellable (swelling) but non-dissolvable microneedles. Among these four systems, only the swellable microneedles are feasible for efficient transdermal delivery of proteins and peptides that require frequent doses. Solid microneedles lack a capacity to load drugs and a diffusion path for loaded drugs to pass through. Although coating medicines on the surface of the needle tips may offer an alternative, the loading capacity is low (approximately 300 ng per needle tip), and moreover, adsorption on solid surfaces often results in protein denaturing. Hollow microneedles, made by deposition of metal vapors onto solid microneedle template or other methods, suffer from poor mechanic strength, low production efficiency, as well as easiness to block. To void blocking the diffusion path, highly sophisticated injection devices are required. Injecting liquids to the dermis layer, the site for microneedle delivery, using conventional injectors will cause overflow of the drug solution. Polymeric dissolvable microneedles are actively studied for delivering vaccines, a kind of medication requires limited administration per year. For transdermal delivery of insulin, a drug requiring multiple doses per day, dissolvable microneedles are unflavored for the deposition of needle tips materials in the skin. Even for infrequent vaccine doses, the development of dissolvable microneedle dosage forms encountered a number of hurdles such as insufficient mechanical strength, difficulty in sterilization, and manufacture inefficiency.

Swellable microneedles are those which are hard and strong enough to penetrate the epidermis layer at dry state, but convert to swollen hydrogel state by absorbing the body fluid in the dermis layer. Hydration of the matrix of the tips of the swellable microneedles enables proteins or peptides pre-loaded in the microneedles to be released across the epidermis and reach the dermis layer. Since the swollen microneedles are still strong enough to be pealed off completely from the skin, polymer deposition is no longer a problem. We name the swellable microneedles as "phase-transition microneedles" and will use this term instead "swellable microneedles" hereafter. Another advantage of phase-transition microneedles is their easiness in sterilization. Since bacteria or viral particles are several orders of magnitude larger than proteins in diameter and cannot be released from the swollen network of the polymeric matrix of phase-transition microneedles, sterilization may be achieved by surface treatment such as ethylene oxide steaming. As a benefit, the product sterilization no longer needs to cover the entire production line, but the packaging step only.

Phase-transition microneedles were fabricated using molding method to date. The molding method comprises casting an aqueous solution of microneedle-forming polymers onto a mold possessing an array of micro-holes, freezing and thawing the casted polymer solution to solidify the microneedles, detaching the microneedle sheet (whereon the microneedles are standing), and drying the sheet. The molding method associates with some limitations, comprising 1) considerable amount of ingredients left on the back sheet which cannot be released to the fluid of dermis layer; 2) inability to load targeted ingredient to particular sections along the microneedle shaft; and more importantly, 3) since the microneedles only occupy approximately 10% of the total area of the back sheet, active ingredients left over take considerable fraction and are not uniformly distributed, which caused unacceptable division between microneedle patches.

In order to produce microneedle patches with practically feasible quality and efficiency, the microneedle patches must have the same amount of drug load, as well as the same drug distribution along the microneedle shaft. It is even better if the active ingredient can be load or distribute along the needle shaft in a designed profile. This is a difficult task for molding methods, in terms of achieving such a section-determined drug loading. Therefore, a new fabrication method without using molds and molding process become necessary. The so-called "3D printing" and its derivatives, such as cumulating or piling up, might be feasible.

The essential step of 3D printing and its derivatives is the way of how the printing fluids turn to be solids at each printing position right out of the printing nozzle. In the case of 3D printing of polymeric microneedles, there are three mechanisms reported to date, rapid polymerization of liquid monomers, rapid cross-linking of polymer solutions, and rapid condensation of heated polymer melts. These methods all involve exposure of medicines to hazardous conditions, i.e. chemical reactions or elevated temperature, thus infeasible, and intensive light. These are unflavored or should be avoided during formulating biologic therapeutics.

Another so-called 3D printing of microneedles relies on drop-by-drop piling up [U.S. Pat. No. 8,192,787]. The first drop of a microneedle-forming polymer solution was injected on a flat sheet, followed by a drying period for the solution to become fairly solidified. Then the second, third, fourth, fifth and sixth drop were added successively on the top of their respective precursors. The 3D printing method is not only very inefficient, but also limited to such a needle shape, like a donut string.

For transdermal administration of biologic ingredients, the rapid conversion of liquid to solid must be achieved under a mild condition. As a practically feasible method for production of microneedle patches, the 3D printing process must be highly efficient, friendly to biologic molecules, and flexible in shaping microneedle tips. The present invention teaches such a 3D printing process.

SUMMARY OF THE INVENTION

This invention teaches a method to produce microneedle patches by printing, injecting, cumulating, or piling up an aqueous solution of microneedle forming materials onto a microneedle supporting sheet. The key mechanisms for the present invention to achieve liquid to solid conversion during printing (or cumulating) polymeric microneedles include 1) rapid freezing the solution of microneedle forming materials; and 2) printing multiple microneedles at the same time. Once the printed microneedle-forming solution is frozen, it will not re-melt but turn to be hydrogel state at room temperature. A polymer solution containing a polymeric component that forms microcrystalline (or nano-crystalline) domains during the freeze-thaw treatment is used as the material to print microneedles. A supporting plate (or sheet) made of a polymer solution containing the same or similar microcrystal-forming polymer will be loaded on a cold sample holder to maintain its frozen state. This operation of variable expression terms is named as 3D printing in the present invention. (U.S. Ser. No. 62/295,166)

The method mentioned before wherein an injection or injecting pump is used to print, inject, cumulate, or pile up, i.e. 3D print, the solution of microneedle-forming materials. Wherein the injection pump is equipped with a nozzle head which has single or multiple micro-holes aligned to an array. The printing nozzle, or array of nozzles for printing multiple microneedles, should be placed in a distance close enough, normally 0.1 to 0.9 mm in distance, to the cold supporting plate to start printing or injecting of the microneedle-forming polymer solutions. The array of nozzles is optionally a nozzle head having multiple micro-holes aligned in an array at a flat plane.

During the printing, injecting, cumulating, or piling up process, the injection/printing rate should be programmed in coordination with up-lifting of the nozzle or the nozzles head with multiple micro-holes from the cold supporting sheet. The shape of the microneedles can be determined by regulating the printing or injecting rate with the rate of elevation of the printing nozzle or array of nozzles (or the nozzle head of multiple micro-holes). The relationship between the printing and lifting rates determines the shape of microneedles. These relations may be expressed and controlled by specific mathematic equations as the control models for movement of the nozzle or array of nozzles. For example, according to these equations, the shape of the microneedles may be a regular cone, alternated fat cone, or their combination look like arrow on waistline. The length of the printed or injected microneedles may also be determined by the distance between the nozzle or array of nozzles where injection is terminated.

The freezing-aided single or multi-points 3D printing may include two or three stages, of which the printing stages may involve respective compositions of the microneedle forming materials. Taking the two stage 3D printing for example, the two different polymer solutions should be added to two respective injecting pumps. The two loaded injecting pumps are mounted vertically with each of the microholes of the nozzle head of the first pump aligned in line with each respective micro-holes of the second pump. After the first injecting pump is used to print the polymer solution 1 to an array of microneedles of a designed length, the sample holder that carries the backing sheet slide on a cold surface below −1° C. to face the nozzle head of the second injecting pump. Then, the polymer solution 2 is printed on the top of each respective microneedles printed by the first injecting pump.

The double or triple printing process may have a series of advantages. For example, only the front part of the microneedle shaft may contact with the dermis layer of the skin where the interstitial fluid becomes available. Double printing may enable the active ingredients to be loaded only in the front section of the needle shaft, and have the base section free of drugs to save the drugs and improve bio-availability. In the case of cosmetic applications, if the entire microneedles are made of hyaluronic acid (HA) for example, some of the polymer will deposit in the micro-holes across the epidermis layer, which will retard the micro-hole closing. Using double printing process, the base section and the front section of the microneedles may be printed consequently with PVA and HA, followed by the above-mentioned freeze-thaw treatment. The section of the microneedle tips that contact with the epidermis layer is therefore the made of the insoluble PVA cross-linked through microcrystalline domains, which can be removed from the skin completely after the HA of the front section of the needle tips has dissolved.

The shortcomings of double or triple 3D printing are mainly that the production process will be complicated accordingly.

The rapid microneedle printing method comprises a drying process, which follows the freezing-aided rapid printing. As a unique feature, the drying process start with a freeze-thaw treatment of the freshly printed microneedle array. To avoid dissolution at room temperature, the polymer matrix of the frozen microneedles must be cross-linked. The cross-linking between the polymer chains, however, must not be achieved through chemical reactions in order to avoid exposing drugs, especially biomedicines, to reaction hazards. The freeze-thaw treatment may induce some water soluble hydrophilic polymers, such as polyvinyl alcohol (PVA) to form microcrystalline (or nano-crystalline) domains at hydrated state. These microcrystalline domains may function as cross-linking junctions through which the polymer chains are cross-linked. The frozen microneedles with cross-linked matrix will no longer dissolve or melt at room temperature, and can therefore be dried by water evaporation.

Some hydrophilic polymers, such as many polysaccharides, do not form sufficient amount of micro- or nano-crystalline domains inside their hydrated matrix by temperature changes. Therefore, the freeze-thaw treatment cannot result in cross-linking between the polymer chains, so that the frozen microneedles formed from these polymers may stand at low temperature but melt at normal temperature. For microneedles printed with these polymers, drying must be carried out below the temperature at which the frozen microneedles dissolve or melt. The drying temperature should also be high enough to ensure that the frozen microneedles to unfreeze. For a viscous aqueous solution of high molecular weight polymers, there is a narrow temperature window wherein microneedles of unfrozen state could still stand by themselves, and the drying process should be carried out within the temperature window. A reasonable scope of this temperature window could be between −5° C. and 5° C., with the best choice to be −2° C. and 2° C. The concentration of the microneedle forming polymer solution is high enough to lower the water freezing point substantially, and the viscosity of the polymer solution is sufficient to maintain a solid state above the freezing point.

Drying of the printed microneedle arrays on the back sheet should be guided to avoid curling due to uneven shrinking along the X-Y plane. To achieve this goal, a fixture that may clamp the back sheet to prevent curling and at the same time to regulate the extent of the shrinking along the X-Y plane should be used.

BRIEF DESCRIPTION OF THE DRAWINGS

The present invention will hereinafter be described in conjunction with the following drawing figures, wherein like numerals denote like elements.

DETAILED DESCRIPTION

Figures 1, 2:
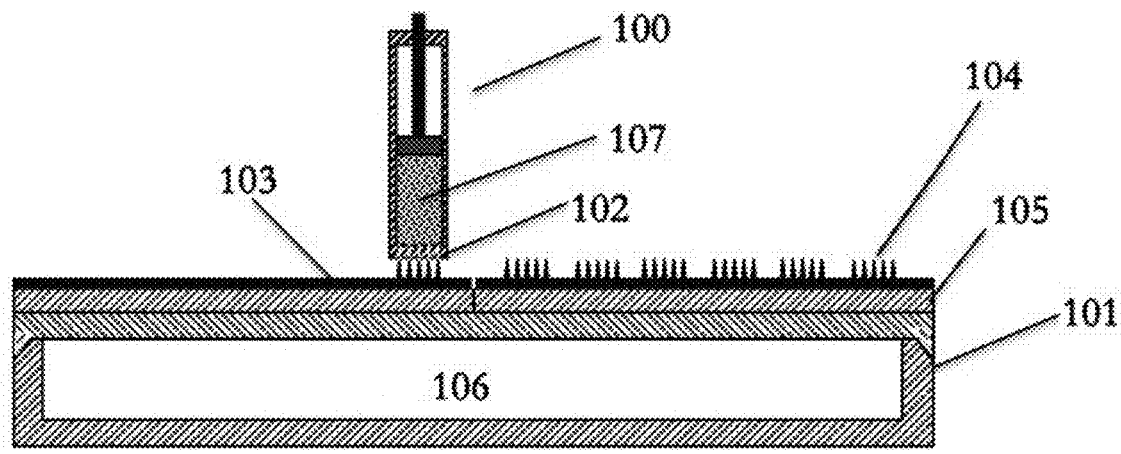
FIG. 1. is a schematic view illustrating the process and apparatus for producing microneedle arrays by rapid 3D printing (or cumulating) method.
FIG. 2. is a chart illustrating needle shapes and respective mathematic models for controlling microneedle printing. Constant "b" needs to be determined on the basis of concrete design and experiments. The mathematic equations are some examples among a large number of variations, so that they should not be used to limit the claims of this invention.

The following detailed description is merely exemplary in nature and is not intended to limit the invention or the application and uses of the invention. Furthermore, there is no intention to be bound by any theory presented in the preceding background of the invention or the following detailed description.

Selecting Microneedle Forming Materials

Selecting the microneedle-forming polymer or polymers is the first step to prepare microneedles using freezing mechanism to convert liquid polymer solution to solid needle tips. One important criterion for the microneedle-forming materials is that the water-soluble polymers must ensure that the frozen microneedles made of the polymer solution do not re-melt at room temperature. To achieve this nature, hydrophilic polymers that form micron or submicron sized crystalline domains by freeze-thaw treatment should be used. The micro- or sub-micro-crystalline domains function as cross-linking junctions that ensure the frozen microneedles to retain in hydrogel state at room temperature. Polyvinyl alcohols over 90% hydrolyzed acetate bonds is one of the examples of such polymers. The supporting plate preferably, but not necessarily, has the same or similar composition of the microneedles to be printed.

Some applications may require the microneedle-forming materials to be delivered into the dermis layer. In these cases, water-soluble microneedle-forming polymers, such as hyaluronic acid (HA) or carboxyl methylcellulose (CMC), should be used. To avoid the microneedles made of these water-soluble polymers to dissolve or melt during the drying process, a low temperature setup, such as a temperature window between −5° C. and 5° C. or −2° C. and 2° C., should be maintained.

As a summary, all water soluble polymers or non-polymeric pharmaceutical excipients may be used as microneedle forming materials to achieve 3D printing of microneedles using the present method. The feasible microneedle forming materials comprise polyvinyl alcohol, polysaccharides, polyethylene glycol, polyvinylpyrrolidone, or other pharmaceutically accepted hydrophilic materials. The polysaccharides mentioned above comprise polyelectrolytes and their salts such as carboxyl methylcellulose, hyaluronic acid, alginate, chitosan, and uncharged polymers such as dextran, starch, and cellulose.

The microneedle forming materials may contain one or multiple biologically or therapeutically active ingredient. The biologically or therapeutically active ingredient may be proteins, peptides, nucleic acids, antibodies, vaccines, and nanoparticles. The proteins and peptides comprise insulin, GLP-1 receptor agonists, calcitonin, parathyroid hormone (PTH), exenatide and other GLP-1 receptor agonist peptides, and other frequently administrating protein and peptide drugs.

Printing Multiple Spots Simultaneously

Typical 3D printing is achieved by scanning a single printing nozzle along a flat layer while injecting the printing materials programly. This 3D printing model does not satisfy efficient production of microneedle patches. For a microneedle patch, since the microneedles are nicely aligned in an array, in another word the positions of each microneedles are fixed, programmed scanning is no longer necessary. Instead, practically feasible production of microneedle patches requires highly efficient 3D printing. This goal can be achieved by printing all the microneedles of a patch at their respective fixed array positions simultaneously.

As shown by the schematic description in FIG. 1, the machinery system for achieving the simultaneous multi-points 3D printing consists only two unit devices, a vertically mounted injecting pump 100 and a cold plate 101 on which the backing sheet of microneedle arrays 104 is supported and cooled. The injecting pump 100 is equipped with a nozzle head 102 of tens or hundreds micro-holes which are nicely aligned to an array. The uniformity of the micro-holes in shape, diameter, surface morphology, as well as their accurate alignment on a one-level plate ensure the microneedles of uniform shape and length to be printed at the same time.

The backing sheet 103 is loaded on a holder 105 made of metal or other good heat conducting materials which contacts with the cold plate, named cold platform 101, and slide to face the spot of microneedle array to the nozzle head of the injecting pump. Once an array of frozen microneedles 104 are printed, the sample holder will be slid to face another spot of the backing sheet to the printer nozzle for printing next array of microneedles. After all the available spots on the backing sheet loaded on the sample holder have been printed, the sheet 103 and the holder 105 will be transferred to a drying process.

Sequential Printing of an Array of Microneedles

Sequential 3D printing of microneedles is achieved using the similar system (FIG. 1) except two or three injecting pumps are used in line. In the case of two step sequential 3D printing, for example, the first pump prints the basal section of the microneedles and the second pump prints the top section on the top of the basal section printed by the first pump. The sample holder is used to face the sequentially printed spots of microneedle arrays to pump 1 and pump 2 consequently. One more such operation will be added for three step sequential printing.

The Factors Affecting Microneedle Shapes

The so-called "microneedle 3D printing" in the present invention may not be necessarily the same as most of 3D printing form functional materials. For one patch of the microneedles, since the needle tips are aligned an array of fixed positions, the printing nozzle do not need to scan along the X-Y plane if each of the microneedle spot is facing a nozzle hole and being printed at the same time. The printing nozzle or the array of the printing nozzles (or a nozzle head having multiple micro-holes) is/are therefore moved along one dimension during the microneedle production. The printing nozzle is moved down to close the printing surface and lifted up while the microneedle-forming materials are injected. Designed microneedle shapes are achieved by the relative rate of the nozzle lifting and the rate of polymer injection (printing). For example, slow nozzle lifting and rapid polymer injecting will result in thick microneedles and vice versa. For a fixed nozzle-lifting rate, adjusting the injection rate of the polymer solution dynamically may lead to designed shape of the microneedles. This process may be described by corresponding equations as the mathematic model of process control. FIG. 2 showed three control equations correlated with respective needle shapes.

While some mathematic equations are provided in FIG. 2, they are only few examples. The flexibility of the rapid 3D printing demonstrated in the present invention allow variety of ways to manipulate microneedle shape, with and without a mathematic description. Some times, none calculation try-out could be more efficient to reach a satisfied needle shape.

The temperature of the backing sheet on which the array of microneedle stands is also critical in determining the microneedle shape. The temperature of the surface of the cold plate is selected between −15° C. and −3° C., with the best temperature selected between −9° C. and −5° C. The temperature fluctuation of cold plate should be limited within 5° C., with more ideal range within 2° C. This temperature range can be controlled by circulating a refrigeration medium through a heat exchange unit or by attaching semi-conductor cooling devices.

Post-Printing Treatment

To improve the characteristics of the printed microneedles such as strength, swelling ratio, and release kinetics of the ingredients loaded in the microneedles, post-printing treatments are necessary or preferred. These post-printing treatments comprise freeze-thaw or repeated freeze-thaw, drying, punching to right sizes and packaging.

For the applications in which water-soluble polymers are used, for which the freeze-thaw treatment is no longer feasible. In this case, the temperature of the drying process should be well controlled within a window at which the printed microneedles are warm up form the frozen state, but still remain self-stand rigidity. The concentration and the viscosity of the microneedle forming polymer solution enable the printed microneedles to self-stand in a non-frozen state. This temperature window should be between −5° C. and 5° C., with the best choice to be −2° C. and 2° C.

Machinery System for Producing Microneedle Patches by Rapid 3D Printing

The system to produce microneedle patches using a rapid 3D printing process consists some essential parts, comprising accurate injecting pump with a nozzle head of multiple micro-holes, a cold plate to load a sample holder to position the back sheet of microneedle arrays to the printing nozzle, and a drying unit of low moisture and controlled temperature. The motion of the injecting pump involves programed up-lifting the pump body from back sheet and injection of the microneedle forming materials in programed rate. Sliding the sample holder to position the back sheet to the printing nozzles can be achieved manually or automatically, while the later is preferred for large-scale production. The site of 3D-printing may be covered by a hood, wherein the humidity is kept below 30% to avoid water condensation on the polymer back sheet on which arrays of microneedles are printed.

The drying unit of the production system should have sufficient capacity to receive microneedle patches printed on the backing sheets, be maintained under a dry condition with relative humidity below 60%, and offers temperature adjustment for the freeze-thaw treatment as well as drying for microneedles of cross-linked matrix and un-cross-linked matrix. The temperature for the freeze-thaw treatment varies between −25° C. and 5° C., and that for the drying process afterwards is maintained between −5° C. and 5° C., with the best choice to be −2° C. and 2° C. In order to achieve the proposed freezing-based process of microneedle printing, an apparatus 106 (FIG. 1) comprising a cold though is necessary. This apparatus, or the future manufacture line, should consist with a cold though to maintain the freezing temperature for the polymer solution, a digitally programmable injector for polymer solutions, a precisely designed injecting nozzle or array of nozzles, a digitally programmable unit for lifting the injector, and a patch holder to position the supporting plate and microneedle arrays. FIG. 1 describes such an apparatus schematically. The patch holders 105 will be transferred along the production line.

A fixture is used to guide the drying process of each microneedle-standing back sheet and prevent curling of the sheet. The fixture should clamp the sheet at its periphery where no microneedles stand. The fixture should provide sufficient force to clamp the sheet to avoid curling, but flexible enough to allow the sheet to shrink along the X-Y plane. The fixture also possesses a stopping edge to regulate shrinking of the sheet to designed size.

EXAMPLES

The examples below provide comprehensible description to help technical workers familiar with the general knowledge and methods to better understand the art of the present invention. The examples should not be used to limit the scope of this invention and its applications.

Example 1

Determining Microneedle Shapes by Printing Process

Figure 3:
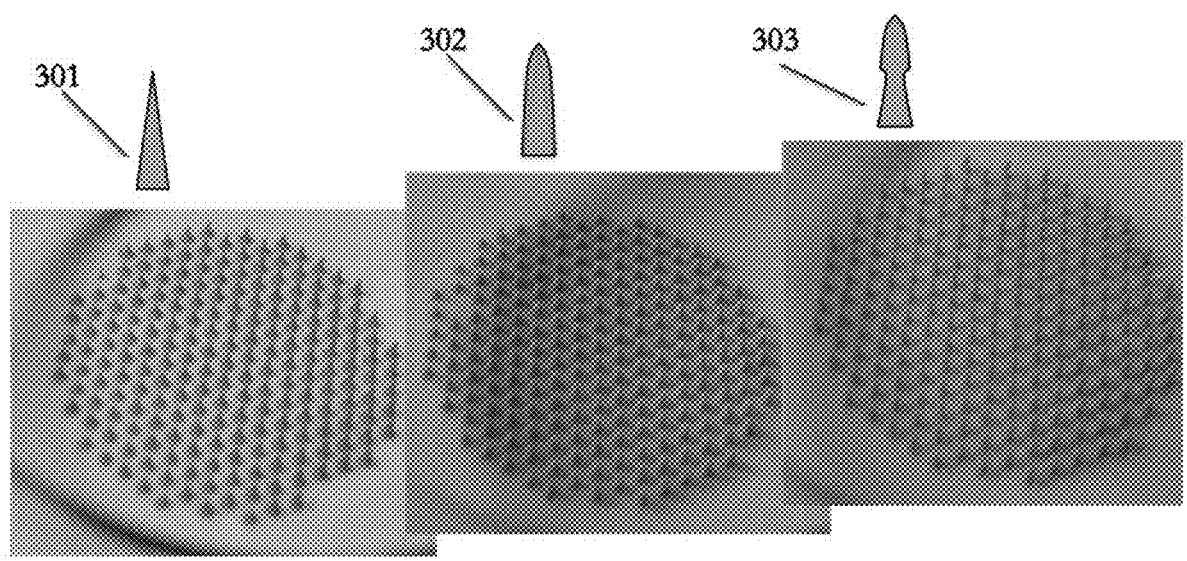
FIG. 3. is a perspective view illustrating arrays of microneedles of various shapes produced by rapid 3D printing using respective input parameters.

A solution 107 containing polyvinyl alcohol (PVA) as the majority mass, polysaccharide, and insulin was added in the injecting pump 100 as shown in FIG. 1, and printed onto a frozen back sheet 103 made of PVA solution. By varying the injection rate and the velocity of the pump lifting, microneedle patches of various needle shapes were printed. The time to complete printing of one arrays of 199 needle tips was within 50 second. Freshly printed microneedle patches of three typical needle shapes were photographed and shown in FIG. 3. The three typical needle shapes are corresponding to those shown in FIG. 2 as regular cone 301, fat cone 302 and arrow on waistline 303. This result indicates that microneedles of desired shapes can be achieved by varying input parameters in the operation program without any modification of the hardware.

Example 2

Printing Hyaluronic Acid Microneedles that Contains No PVA

A hyaluronic acid (HA) solution containing no PVA (the polymer that forms microcrystalline domains for cross-linking) was loaded in the injecting pump and printed onto a frozen PVA back sheet. The HA microneedles well stood on the PVA back sheet without falling off, suggesting that HA microneedles could well attach on the PVA sheet.

Example 3

Drying Printed Microneedle Patches

A drying system consisting three compartments of −20° C., −1° C. and 1° C., respectively, was used dry printed microneedle patches. First, the freshly printed microneedle sheets each of which carries six arrays of microneedles were placed in the compartment of −20° C. together with the metal sample holder overnight (at least 2 hours) for deep-freezing. Then, the microneedle sheets were moved to compartment −1° C., wherein the humidity was below 40%, for primary drying for 4-6 hours. During this thawing process, the entire microneedle shaft remained solid state, and the tip end became partially dry. Since the microneedles with partially dried tip will no longer melt at refrigeration temperature, each of the sheets was transferred the metal sample holder to a Teflon fixture, and placed in compartment 1° C. for further drying overnight. Finally, the sheet of microneedles clamped on the Teflon fixture was transferred from compartment 1° C. to a desiccator for through drying overnight.

As a laboratory setup, the drying time of Example 3 was not well designed but was rather arbitrary. For scaled production, the drying process can be facilitated by circulating dry air over the microneedle sheets, and the time for complete drying may be shortened.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

The invention claimed is:

1. A method for 3D printing microneedle patches, comprising:
   a) load an aqueous solution of microneedle forming materials in an injection pump;
   b) print, inject, or pile up the aqueous solution of the microneedle forming materials from the injection pump to a supporting sheet or plate, the supporting sheet or plate is at a temperature at or below the freezing point of the aqueous solution, to form frozen standing microneedles;
   c) dry the microneedles formed in step b).

2. The method of claim 1, wherein designed microneedle shapes can be achieved by adjusting the injection rate of the aqueous solution of the microneedle forming materials and a lifting velocity of the injection pump.

3. The method of claim 1, wherein said injection pump mount is mounted with a nozzle of single or multiple micro-hole(s).

4. The method of claim 3, wherein the micro-holes of the multiple micro-hole nozzle are aligned to an array.

5. The method of claim 1, wherein the microneedle supporting sheet or plate is formed from the same materials of the microneedles.

6. The method of claim 1, further comprising
   loading the microneedle supporting sheet or plate on a sample holder made of metal,
   carrying the microneedle supporting sheet or plate and printed microneedle by the sample holder; and
   transferring the microneedle supporting sheet or plate and printed microneedle to a drying unit.

7. The method of claim 6, wherein the sample holder is laid on a cooling platform for keeping the supporting sheet or plate in the frozen state, and the sample holder is configured to slide on the cooling platform in order to face the spot of printing microneedle array to the nozzle.

8. The method of claim 1, wherein the printed microneedles are dried by one of the two procedures as:
   a) treat the frozen microneedles through one or more freeze-thaw cycle(s) to crosslink their matrix by forming microcrystalline domains as crosslinking junctions prior to drying;
   b) drying the frozen microneedles between −5° C. and 5° C. without the freeze-thaw pre-treatment.

9. The method of claim 1, wherein the drying process comprises using a fixture to clamp the supporting sheet or plate to prevent curling of the sheet or plate.

10. The method of claim 1, wherein the microneedle-forming materials are selected from polyvinyl alcohol, polysaccharides, polyethylene glycol, polyvinylpyrrolidone.

11. The method of claim 10, wherein the polysaccharides include their polyelectrolytes and their salts non-charged polymers.

12. The method of claim 11, wherein the polyelectrolytes and their salts are selected from carboxyl methyl cellulose, hyaluronic acid, alginate, chitosan; and the uncharged polymers are selected from dextran, starch, and cellulose.

13. The method of claim 1, wherein the microneedle forming materials carry at least one biologically or therapeutically active ingredient.

14. The method of claim 13, wherein the biologically or therapeutically active ingredient is selected from proteins, peptides, nucleic acids, antibodies, vaccines, and nanoparticles.

15. The method of claim 14, wherein the proteins and peptides comprise insulin, GLP-1 receptor agonists, calcitonin, parathyroid hormone (PTH), exenatide, and other frequently administrating protein and peptide medicines.

16. The method of claim 1, wherein the said injection pump is driven through an operation program which determines the shape of the microneedles by adjusting the rate of material injection and velocity of the pump lifting.

17. The method of claim 1, wherein the step b) may comprises two or more steps for which different microneedle forming material(s) and different injection pump(s) is used to print on the top of previously printed spots of the array to produce microneedle shafts of which each section is formed from different materials.

18. The method of claim 1, wherein microneedles made by a stepwise printing have their front part only loaded with a therapeutic active ingredient or cosmetic ingredient in order to improve bioavailability.

19. The method of claim 7, wherein the temperature of the cooling platform is maintained between −15° C. and −3° C.

20. The method of claim 1, wherein step b) is carried out inside an isolation hood in which humidity is adjusted and controlled, the humidity inside the isolation hood is maintained at 30% or below.

* * * * *